United States Patent
Degner et al.

(10) Patent No.: US 11,280,726 B2
(45) Date of Patent: Mar. 22, 2022

(54) ASSEMBLY AND METHOD FOR MEASURING A SUBSTANCE CONCENTRATION IN A GASEOUS MEDIUM BY MEANS OF ABSORPTION SPECTROSCOPY

(71) Applicant: SENSATRONIC GMBH, Wismar (DE)

(72) Inventors: Martin Degner, Reddelich (DE); Hartmut Ewald, Rostock (DE)

(73) Assignee: SENSATRONIC GMBH, Wismar (DE)

( * ) Notice: Subject to any disclaimer, the term of this patent is extended or adjusted under 35 U.S.C. 154(b) by 123 days.

(21) Appl. No.: 16/563,345

(22) Filed: Sep. 6, 2019

(65) Prior Publication Data

US 2020/0033257 A1      Jan. 30, 2020

Related U.S. Application Data

(63) Continuation of application No. PCT/EP2018/053663, filed on Feb. 14, 2018.

(30) Foreign Application Priority Data

Mar. 10, 2017 (EP) ..................... 17160250

(51) Int. Cl.
*G01N 21/3504* (2014.01)
*A61B 5/00* (2006.01)
(Continued)

(52) U.S. Cl.
CPC ....... *G01N 21/3504* (2013.01); *A61B 5/0075* (2013.01); *A61B 5/0836* (2013.01);
(Continued)

(58) Field of Classification Search
CPC ............. G01N 21/3504; G01N 21/314; G01N 33/497; G01N 2021/3536; G01N 21/37;
(Continued)

(56) References Cited

U.S. PATENT DOCUMENTS 4,011,859 A * 3/1977 Frankenberger ..... A61B 5/0836
600/532
4,618,771 A    10/1986 Farren
(Continued)

FOREIGN PATENT DOCUMENTS

CN     104755147 A  *  7/2015  ........... G01N 21/532
KR     20160063704 A     6/2016
(Continued)

OTHER PUBLICATIONS

Espacenet English translation of KR 20160063704 (Year: 2016).*
(Continued)

*Primary Examiner* — Mohamed K Amara
(74) *Attorney, Agent, or Firm* — Murtha Cullina LLP

(57) ABSTRACT

An assembly and a method for measuring a gas concentration by means of absorption spectroscopy, in particular for capnometric measurement of the proportion of $CO_2$ in breathing air in which IR light from a thermal light source is guided through a measuring cell with a gas mixture to be analyzed, and the concentration of the gas to be measured that is contained in the gas mixture is determined by measuring an attenuation of the light introduced into the measuring cell caused by absorption by the gas to be measured. The thermal light source is designed as an encapsulated micro-incandescent lamp with a light-generating coil.

15 Claims, 5 Drawing Sheets

(51) Int. Cl.
 *A61B 5/083* (2006.01)
 *G01N 21/31* (2006.01)
 *G01N 33/497* (2006.01)

(52) U.S. Cl.
 CPC ......... *G01N 21/314* (2013.01); *G01N 33/497* (2013.01); *G01N 2021/3536* (2013.01)

(58) Field of Classification Search
 CPC ................. A61B 5/0075; A61B 5/0836; G01J 2003/1213; G01J 3/0205; G01J 3/10; G01J 3/427; G01J 3/0216; G01J 3/42
 See application file for complete search history.

(56) References Cited

U.S. PATENT DOCUMENTS

| | | | | |
|---|---|---|---|---|
| 4,648,396 A * | 3/1987 | Raemer | ................ | A61B 5/0836 128/204.22 |
| 5,092,342 A | 3/1992 | Hattendorff et al. | | |
| 5,445,160 A | 8/1995 | Culver et al. | | |
| 5,464,982 A | 11/1995 | Drucker et al. | | |
| 5,811,812 A * | 9/1998 | Williams | ................ | G01N 21/61 250/339.13 |
| 5,942,755 A * | 8/1999 | Dreyer | ................ | G01N 21/3151 250/339.13 |
| 6,277,081 B1 | 8/2001 | Susi et al. | | |
| 6,331,704 B1 * | 12/2001 | Owen | ................ | G01N 15/0205 250/227.22 |
| 6,632,402 B2 * | 10/2003 | Blazewicz | ......... | G01N 21/6408 422/84 |
| 6,990,980 B2 * | 1/2006 | Richey, II | ........... | A61M 16/024 128/204.18 |
| 7,152,598 B2 * | 12/2006 | Morris | .............. | A61M 16/0069 128/204.23 |
| 7,235,054 B2 * | 6/2007 | Eckerbom | .......... | G01N 21/3504 422/84 |
| 7,335,164 B2 * | 2/2008 | Mace | .................... | A61B 5/083 422/84 |
| 7,473,229 B2 * | 1/2009 | Webber | ................ | A61B 5/0836 422/84 |
| 7,967,759 B2 * | 6/2011 | Couvillon, Jr. | ..... | A61B 1/00055 600/529 |
| 8,083,684 B2 * | 12/2011 | Palatnik | ................. | A61B 5/742 600/532 |
| 9,295,410 B2 * | 3/2016 | Weckstrom | ........... | G01F 1/3218 |
| 9,950,129 B2 * | 4/2018 | Glenn | .................... | A61B 5/087 |
| 10,976,240 B2 * | 4/2021 | Deguchi | .................. | G01J 3/10 |
| 2006/0263256 A1 * | 11/2006 | Koshel | ............... | G01N 21/3504 422/83 |
| 2008/0185524 A1 * | 8/2008 | Kanstad | ............. | G01N 21/3504 250/338.5 |
| 2008/0231857 A1 * | 9/2008 | Depeursinge | ...... | G01N 21/7703 356/437 |
| 2009/0027759 A1 * | 1/2009 | Albahri | ..................... | E06B 9/24 359/277 |
| 2009/0296771 A1 * | 12/2009 | Boehm | ................ | G01N 21/552 374/19 |
| 2010/0194914 A1 * | 8/2010 | Jones | ...................... | H04N 7/185 348/222.1 |
| 2011/0090505 A1 * | 4/2011 | Kuze | .................... | G01N 21/314 356/437 |
| 2011/0147592 A1 | 6/2011 | Martin | | |
| 2016/0231244 A1 * | 8/2016 | Camargo | ............... | G01N 21/61 |

FOREIGN PATENT DOCUMENTS

| | | |
|---|---|---|
| WO | 03060490 A | 7/2003 |
| WO | 2007091043 A1 | 8/2007 |

OTHER PUBLICATIONS

Corman et al. "An optical IR source and CO2 chamber system for CO2 Measurement", J. Microelectromechanical systems, 9, (2000). (Year: 2000).*

Wang X et al. "High performance CO2 measurement based on pressure modulation," Procedia Engineering, Elsevier, Amsterdam, NL, vol. 5, Jan. 1, 2010, pp. 1208-1211, XP027483885.

International Search Report issued in corresponding PCT Application No. PCT/EP2018/053663, dated Jul. 18, 2018, pp. 1-8.

* cited by examiner

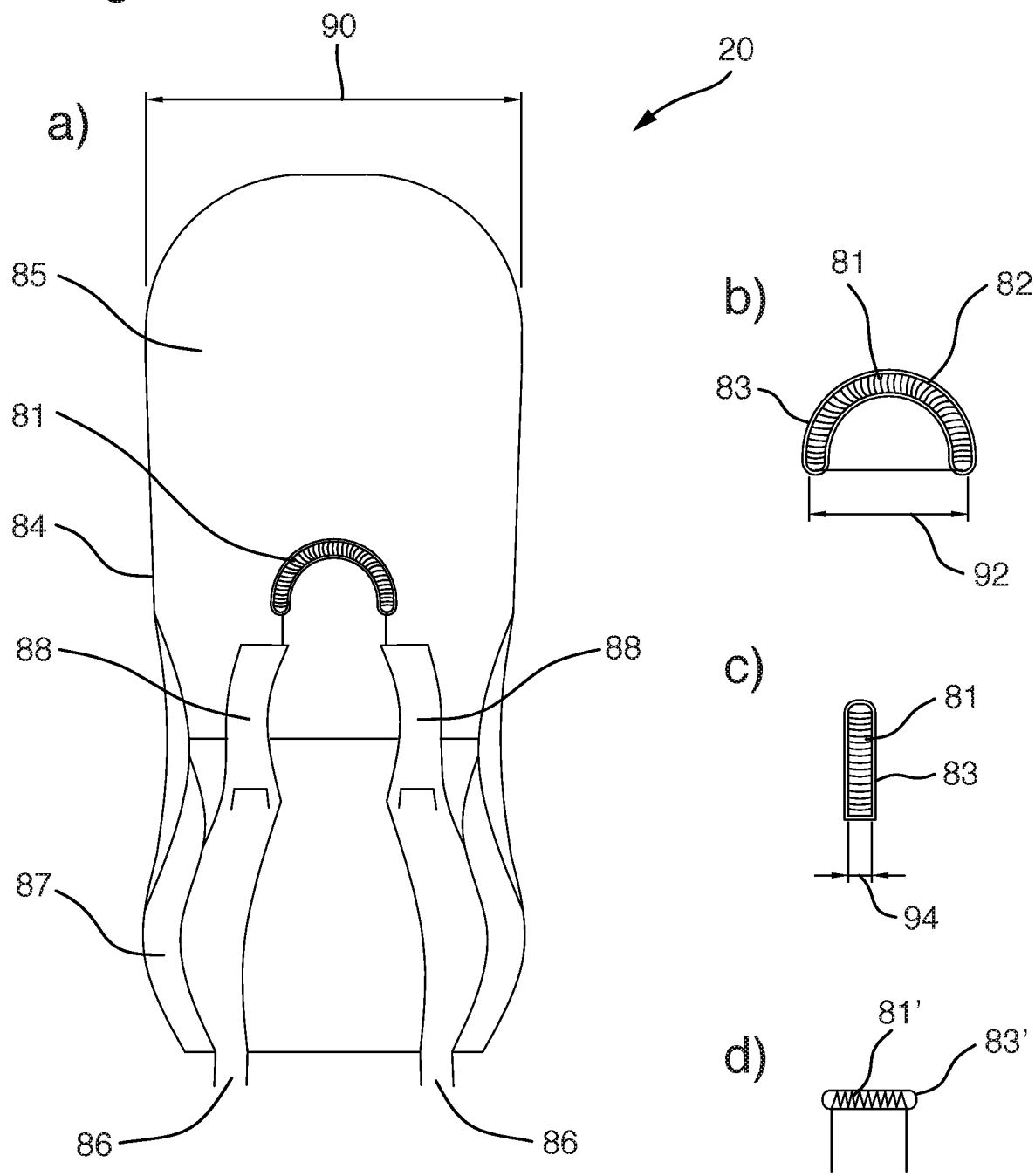

ASSEMBLY AND METHOD FOR MEASURING A SUBSTANCE CONCENTRATION IN A GASEOUS MEDIUM BY MEANS OF ABSORPTION SPECTROSCOPY

CROSS REFERENCE TO RELATED APPLICATIONS

This application is a continuation application of and claims priority to PCT Application No. PCT/EP2018/053663, filed Feb. 14, 2018, which is a PCT Application of and claims priority to EP patent application number 17160250.1, filed on Mar. 10, 2017, the entire contents of which are incorporated herein by reference.

FIELD

The invention relates to an assembly and a method for measuring a gas concentration by means of absorption spectroscopy, in particular for capnometric measurement of the proportion of $CO_2$ in breathing air.

BACKGROUND

The basic principle of such measurements is known. Light, or infrared light (IR) from a thermal light source in the case of measuring $CO_2$, is guided through a measuring cell with a gas mixture to be analyzed, and the concentration of the gas to be measured that is contained in the gas mixture is determined by measuring an attenuation of the light introduced into the measuring cell from being absorbed by the gas to be measured.

The attenuation of the emitted light depends exponentially on the concentration, or respectively density of the absorbent gas, the wavelength-dependent absorption coefficient of the gas, and the length of the measuring path in which the light crosses the gas to be measured. The measurement of the attenuation of the light by absorption requires the knowledge of the amount of the light radiated into the measuring cell and coupled out of the measuring cell. For this reason, two measurements are always needed, i.e., on the one hand the measurement of the amount of light of the light attenuated by being absorbed in the measured gas after passing through the measuring cell and, on the other hand, the measurement of a quantity as a reference measurement which is representative of the radiated amount of light.

This reference measurement can be a direct measurement of the light intensity or light quantity at the light source, wherein a portion of the light from the source is detected which is not used for measuring gas but is nonetheless proportional to the amount of light for gas measurement. The advantage of this is that a direct measurement of the radiated light intensity is problematic since the light used for reference measurement is only proportional and not identical to the light used for the gas measurement. The proportional dependency can change over the course of time since the light for the reference measurement has not passed through the same optical path as the light for absorption measurement and accordingly does not possess additional absorptions, for example from impurities. Developments over the long term such as increasing soiling of the measuring window of the measuring cell can also cause a systematic drift of the absorption measuring results.

An alternative assembly uses reference light that also passes through the measuring cell but lies within a wavelength range in which the gas to be measured is scarcely or not absorbed. The reference light therefore only undergoes the absorption that is caused by impurities or other systematic sources, and to which the light within the wavelength range of absorption of the gas to be measured is also subjected. With the exception of wavelength-dependent, i.e., dispersive, effects increasing soiling in the measuring cell for example then affects the absorption measurement in the same way as the reference measurement. In the comparison of the two measurements, these contributions largely cancel each other out so that corresponding systematic effects that negatively influence the measuring results are largely minimized.

In the field of capnometry, infrared light is used since the gas $CO_2$ has a strong absorption band at approximately 4.26 µm, i.e., within the middle infrared range. The present invention is therefore particularly applicable in the field of capnometry but can also be used for other applications in which absorption measurements, in particular within the infrared range, are performed. Capnometry is a monitoring procedure used in medicine and provides information on the patient's status in the field of emergency services, in clinics, at-home care and sports medicine.

Capnometers are generally small mobile devices, sometimes with a unit that can be handheld for parameterizing and visualizing, wherein in many cases, the sensor unit is also contained in the manual device in side stream applications. Such capnometers can also be integrated as ready-to-use assemblies in larger devices such as ventilators, metabolic monitors, inter alia.

Capnometers detect the $CO_2$ curve of the respiration of a patient. This measurement is performed either in the so-called main stream method or in the so-called side stream method. In the main stream method, generally a sensor is placed in the proximity of the breathing mask of the patient that measures the $CO_2$ concentration through a cuvette in the breathing hose. In the side stream method, a cuvette with a thin suction hose is attached in the breathing gas channel, part of the breathing air is conveyed through the suction hose to a sensor module and measured there with a certain dead time.

Given the applications, especially in the field of emergency services and home care as well as sports medicine, sensor modules should be small, light and robust in order to withstand vibration, and have a low power consumption because mobile use without an external power supply is frequently necessary. Currently available main stream sensors only have a battery life of 4 to 6 hours. For capnometric measurements, a precision of ±0.43% $CO_2$+8% of the measured value is required according to the ISO 80601-2-55 standard. Devices on the market generally significantly exceed these requirements. Furthermore, a measuring interval of 10 ms to 40 ms, preferably up to 25 ms, with measured values that are independent from each other should be implemented for a resolution of the respiratory curve even with a higher respiratory rate of up to 150 breaths per minute which may occur inter alia with newborns. Given this temporal resolution, it becomes possible to reliably determine the endexpiratory value, which is a medical parameter. Especially for time-critical applications such as emergency medicine, quick measuring readiness after a cold start is also desired, i.e., a short so-called startup time. In this regard, conventional systems sometimes require several minutes in order to reach the necessary operating temperature. Moreover, economical and easy production is desired.

Filter wheel assemblies are known for example as marketed by Massimo Inc. and for example disclosed in WO 03/060490 A. These assemblies comprise a mechanically rotating wheel in the optical beam path with at least two filters for the gas absorption and the reference wavelength, and also with a region in which the light is completely blocked. Blocking allows a measurement of darkness that is used for offset compensation by the receiving unit. In this case, the measuring principle is realized that the measuring wavelength and the reference wavelength pass through the same optical path. The light also does not have to be distributed to different paths. This is a time multiplex measuring method, and the use of mechanically moved components in the optical beam path may be sensitive to vibration.

An assembly with spectral beam dividers is for example known from U.S. Pat. Nos. 5,464,982 A and U.S. Pat. No. 5,092,342 A, wherein modulated light is distributed at the receiving side to two or more detectors for the gas absorption and for the reference wavelength. This is a typical spectroscopy assembly as well, in which one light source is used and a high light yield is achieved since the light is split up wavelength-selectively rather than geometrically. Losses occur however from the damping in the transmission region of the filter. Simultaneous measurement occurs in the absorption wavelength and the reference wavelength so that there are no restrictions with regard to the time characteristic and the target quantity. It is comparatively involved to integrate more than two wavelengths to measure several measuring gases. A beam divider filter may be necessary that can be expensive. For the sake of an offset compensation, the source can also be modulated in this case.

Another basic type of assembly is geometric parallel measurement. In this case, the light from the light source is guided to a plurality of unfiltered receivers without beam division. For this, different optical light paths are used for each measuring path, i.e., the gas path and reference path. This also means that in absorption measurement and reference measurement, different regions of the source and different transmission paths are used by the measuring devices. This results in ambiguities as to which effect the geometric division and which effect the actual absorption by the measuring gas has on the measurement. These ambiguities can yield systematic measuring errors. These assemblies are for example known from U.S. Pat. Nos. 4,618,771 A and 6,277,081 B1 and are used rarely in practice, for example by Goldwei (China). The very simple assembly of simultaneously measuring absorption and reference and omitting mechanically moved components has advantages in this case. However, geometric parallel measurement suffers from worse suppression of interferences with respect to spatial fluctuations by the source, different light transmission to the two detectors, for example by the formation of condensate in the cuvette, and by a reduced light yield from the non-directional illumination of the receivers. In this case as well, the source can be additionally modulated in the interest of offset compensation.

Another measuring principle includes a wavelength shift of the light source. The maximum of the emission spectrum of a usually narrowband light source is modulated alternatingly over time, usually thermally induced, between regions of a stronger and weaker absorption of the target quantity, such as $CO_2$. Accordingly, in the temporal sequence of the measured values, alternating values with a high influence on the target quantity (gas measurement) and with a slight influence (reference measurement) are available. Typically, lasers are used as a light source for this type of measurement, such as diode lasers. In the field of $CO_2$ climate measurement, a measuring procedure has become established in which an LED is spectrally modulated, as described in WO 2007/091043 A1, for example. This method only uses an optical path, a light source and a detector, and does not require an optical filter since the narrowband light source is spectrally modulated. These narrowband light sources have a low power consumption in comparison to the required emission; nonetheless, the thermal modulation of these light sources can also be very energy-intensive. This is a time multiplex measurement, i.e., the modulation of the emission spectrum must be faster than the lowest time constant of the measured quantity. In capnometry, this restriction can be problematic; in the field of climate measurement, this is not a problem. Controlling, implementing the measuring method and producing the sensors are very complex, in particular with LEDs and photodiodes. Furthermore, it is difficult to fill out the large temperature range necessary for modulation, and the measurement is vulnerable to temperature gradients. The light yield is reduced by the modulation, which negatively affects the signal-to-noise ratio (SNR).

In the case of capnometry, conversely, thermal emitters are primarily used as a light source for optical $CO_2$ measurement in the middle infrared (MIR) since the main absorption of $CO_2$ is at approximately 4.26 μm. These thermal emitters are economical and robust. Light sources in capnometry assemblies should achieve a high emission performance to enable sufficient light intensity for a favorable SNR in the receivers. Detectors in the middle infrared range frequently have high thermal inherent noise; consequently, a strong useful signal is required for a good SNR. Likewise, a strong useful signal is needed in order to reach the required concentration resolution for the given short measuring time of 10 ms to 25 ms.

The physics of the thermal emitter dictate that the emitted intensity only depends on the temperature of the emitter and other constants such as the Stefan-Boltzmann constant and the emissivity. Increasing the overall emitted optical performance can only be achieved by increasing the emission area when using a maximum possible light source temperature and with a highest possible emissivity. These parameters are technically limited. In practice, a large-area filament emitter or surface emitter with an active emitting area of more than 1 mm$^2$ is typically used in capnometry at an emission temperature that is frequently 400° C. to 600° C. For example with an emission temperature of approximately 410° C., the maximum emission is 4.26 μm, i.e., at the $CO_2$ absorption line. In addition, the corrosion of the thermal emitter is limited due to this comparatively low temperature, which is advantageous for the longevity of light source that is frequently not protected by an evacuated glass bulb. A glass bulb is omitted in order to prevent additional absorption loss from the glass.

Such large-area emitters without an evacuated glass bulb however require a great deal of electrical power in order to achieve the required emitter temperature, typically more than 300 mW with capnometers. Moreover, a large-surface emitter leads to a long startup time, for example between 30 and 150 seconds in spite of an increase in power after the start.

The large thermal mass also makes the emitter sluggish so that only a slow modulation rate is possible with a time constant that is greater than that of the target quantity. Consequently, measurement is impossible in AC mode for offset compensation, in particular when the breathing is fast. The endexpiratory value is determined only imprecisely. With a thermally induced wavelength shift, it is difficult and expensive to implement the functionality of this measuring principle for the ambient conditions in capnometry with regard to the temperature range and temperature gradient.

Another characteristic of thermal emitters (black bodies) is that they have a Lambertian radiation characteristic which, in combination with a large emission surface, means that the light cannot be conducted efficiently and without loss to one or more detectors, even with bundling optical systems. A majority of generated radiation is therefore not used for measurement, which is problematic in terms of energy.

Compensation of the thermal drift of the receivers and suppression of the influence of other thermal radiation sources on the measuring signal, such as the housing temperature and sensor heating, can be achieved in the context of a so-called AC mode by amplitude modulation of the light while measuring transmission, or amplitude modulation is used that is generated by a filter wheel or chopper wheel. The low modulation frequency of large-surface thermal emitters is problematic with electronic modulation since concomitant measurement is imprecise at faster respiratory rates. Mechanical modulation is contrastingly mechanically liable to disruptions. In other embodiments, the light is not modulated. This results in significant measuring errors from drift and parasitic thermal radiation. Such sensors are unsuitable for capnometry.

In corresponding applications, thermopile detectors are generally used. These are large-surface in order to detect as much light as possible in the structure. However, they are quite noisy so that the required signal filtering leads to low limit frequencies of the detectors, whereby the frequency in AC mode is also limited. This also affects the potential rotation speed in a filter wheel structure. Alternatively, pyroelectric detectors are routinely used that are however much more expensive.

SUMMARY

Contrastingly, the object of the present invention is to provide an assembly and a method for measuring a gas concentration, in particular for the capnometric measurement of the proportion of $CO_2$ in breathing air, that improves use in the mobile sector and in the emergency sector with sufficient measuring precision and measuring speed.

This object is achieved by an assembly for measuring a gas concentration by means of absorption spectroscopy, in particular for the capnometric measurement of the proportion of $CO_2$ in breathing air, in which IR light is guided from a thermal light source through a measuring cell with a gas mixture to be analyzed, and the gas concentration of a gas to be measured that is contained in the gas mixture is determined by measuring an attenuation of the light introduced into the measuring cell caused by absorption by the gas to be measured, wherein the assembly has an optical beam path with a thermal light source that generates IR light, the measuring cell that can be filled or is filled with the gas mixture, and a measuring path for the light generated by the thermal light source, one or more sensors as well as one or more bandpass filters that are upstream from the one or more sensors, wherein the assembly furthermore comprises an evaluation apparatus that is designed to determine the gas concentration to be measured from the attenuation of the IR light in the measuring cell, wherein at least one bandpass filter is designed to transmit within a measuring wavelength range in which the gas to be measured absorbs IR light, and at least one bandpass filter is designed to transmit in a reference wavelength range in which the gas to be measured does not absorb IR light or only absorbs a slight amount in comparison to the measuring wavelength range, which is developed in that the thermal light source is designed as an encapsulated micro-incandescent lamp with a light-generating coil.

Within the context of the assembly according to the invention, these are quasi-punctiform light sources. Due to their low thermal mass, a high measuring rate is achievable, the startup time is significantly reduced in comparison to large-surface thermal emitters, and very little power is required to achieve high spiral-wound filament temperatures. Given the low required power, the battery life for a corresponding measuring device, in particular a capnometer, is significantly increased. All of this ensures that a corresponding assembly is optimally suitable for mobile use and in emergency medicine. Since the emission occurs within a very small geometric region, the loss of emitted light is also very slight, so that a very high luminous efficiency is achieved on the employed detectors which also further reduces the energy consumption. Accordingly, a small and lightweight light sensor with a long battery life is feasible. Additional advantages are that no mechanically moved components are used in the optical beam path, and a robust and economical measuring assembly is therefore achievable.

The basic concept of the present invention is that a small, punctiform, or respectively quasi-punctiform thermal light source is used with a comparatively high temperature and low-loss optical imaging of the source on small, in particular quasi-punctiform detectors such as photodiodes. The emission range is preferably much less than 1 $mm^2$. With micro-incandescent lamps, a spiral-wound filament, or respectively a filament within an area of for example 0.2 mm×0.5 mm can be wound, i.e., an area of 0.1 $mm^2$ can be covered. Such a small coil is arranged, or respectively encapsulated in a glass bulb that is evacuated or filled with an inert atmosphere, which protects the coil from corrosion. The encapsulation is necessary given the higher temperatures that may be used. This makes possible a high temperature of the thermal emitter, and consequently a high light intensity within the MIR range as well. This facilitates a good signal-to-noise ratio. Given the assembly in the evacuated glass bulb, a lower heat exchange between the emitter and the environment also results, and therefore lower power loss, as well as mechanical protection and a holder which is useful for production.

To minimize power loss from an excessive extension of the light source, it is advantageously provided that the encapsulation of the micro-incandescent lamp has a diameter of less than 2 mm, in particular less than 1.5 mm, in particular less than 1 mm. In addition or alternatively, the greatest linear distance between two points of the coil is advantageously less than 1 mm, in particular less than 0.5 mm. By appropriately selecting the coil geometry, a very high emitted power is achievable within a very small overall volume of the coil. Furthermore it is additionally or alternatively advantageous if an envelope of the coil in a direction of projection in which the envelope assumes a maximum envelope projection surface has a maximum envelope projection surface of less than 0.1 $mm^2$, in particular less than 0.02 $mm^2$. This dimension that relates to the surface in a projection from a viewing direction in which the projection of the coil on the plane perpendicular to the viewing direction is at a maximum also ensures an advantageous compactness of the light-generating coil.

Preferably, the sensor or sensors are designed as infrared-sensitive photodiodes whose sensitive surface is in particular less than 1 $mm^2$, in particular less than 0.15 $mm^2$. Such small-surface photodiodes have less of a thermal noise load. Moreover, the light emitted by the quasi-punctiform light source can be focused very easily onto the small-surface infrared sensors by optical components. This yields a good signal-to-noise ratio. The components are furthermore economical and robust so that an economical and robust solution is also available with respect to the sensors.

Typical useful photodiodes have a small detector surface, for example approximately 0.35 mm×0.35 mm, i.e., a surface of 0.1225 $mm^2$ which is on the scale of the radiating surface of the light source used according to the invention. Optical point imaging can thus be realized therewith. The small detectors have a high cut-off frequency so that the required measuring rate can be realized without any problems. In comparison to thermopiles and pyroelectric detectors, small photodiodes have a limited spectral sensitivity and are thus less sensitive to interfering thermal radiation sources.

In one advantageous development, a control apparatus is included that is designed for power-controlled driving and/or modulation of the micro-incandescent lamp, wherein the control apparatus is designed to form a product from current measured at the micro-incandescent lamp and measured voltage in order to determine an actual value of the emitted power, and/or is signal-linked to a photodiode arranged in the micro-incandescent lamp that receives a part of the light generated by the micro-incandescent lamp. Even though many filament sources are normally controlled by their voltage, voltage control, given the temperature dependency of its inner resistance, is less suitable for providing constant and reproducible power output than power control. The power consumption and the absorbed electrical power associated therewith as well as the emitted optical power are accordingly thus also dependent on the temperature of the spiral-wound filament. This is clearly revealed in particular when starting up the source after a cold start and when there are changes to the operating point. Accordingly, power control of the filament source is recommendable for a so-called AC mode.

For power control, it is possible to electronically detect and multiply the current and voltage of the radiation source and use this product as an actual quantity for control. A particularly fast control of the power of the light source that is useful for modulating the light source can be achieved by detecting current and voltage in an analog manner and multiplying them in an analog manner. Accordingly, a purely analog controller can then also be used which has advantages in terms of speed and low cost. Alternatively, a digital realization of product formation and control is also possible.

In an alternate implementation of power control, part of the emitted radiation power is detected as free as possible from optical interference sources by means of a sensor such as a photodiode, preferably a low-noise economical VIS or NIR photodiode. The photocurrent generated in the photodiode is directly proportional to the detected optical performance. Accordingly, the amplified signal of the photocurrent can be used as an actual value for controlling the optical performance. This solution requires blocking out outside light as much as possible. It must furthermore be ensured that a representative portion of the emitted light is detected and used for controlling.

In a preferred assembly, the IR light is guided bundled through the measuring cell and distributed to two or more sensors after passing through the measuring cell by means of a spectrally neutral optical plane-parallel or curved transmission or reflection lattice, wherein the transmission lattice or reflection lattice has in particular a lattice constant that is less by a factor of 30 or more, in particular by a factor of 50 and more than a diameter of a light spot on the transmission and reflection lattice. The "light spot" in this case is understood to be the light spot that is generated by the light which is emitted by the micro-incandescent lamp and passes through the optical path to the lattice. A lattice constant of 300 µm or less, in particular of 50 µm or less, is advantageous. This distribution by a spectrally neutral lattice ensures that all the light of both the absorption wavelength as well as the reference wavelength passes through the same optical path until being distributed and therefore does not suffer from any systematic differences in absorption apart from the absorption to be measured in the measuring gas. By means of the spectrally neutral lattice, all of the light that has passed through the measuring cell independent of the respective wavelength is then distributed into two or more paths that are spatially separate from each other and is guided to detectors, or respectively detector units that are separate from each other. Each detector unit can for example have one detector and one optical bandpass filter. These should have different spectral sensitivities so that the received a light on one detector is strongly dependent on the absorption of the measured quantity such as $CO_2$, and the light received by the other detector, the reference detector, is essentially independent therefrom.

Furthermore, the spectral sensitivity ranges of the detector units should be as close as possible to each other so that effects from spectrally dependent, i.e., dispersive, broadband interferences such as temperature-dependent optical dispersion, or the spectral change of the emission characteristic of a thermal source caused by a temperature change, do not have an effect or only a scarcely different effect on the detected signals. Interferences of the transmission in the optical path that are broadband relative to the distance between the two sensitivity ranges of the filters, broadband extraneous light and intensity fluctuations in the light source can be suppressed by offsetting the received detector signals against the absorption measurement signal. Accordingly, the precision of the measurement of the target quantity, such as the concentration of $CO_2$, is significantly increased.

It is advantageous in this context if the light components detected by the detector units essentially originate from the same point of origin of the light source, and essentially the same optical path is followed from the source until being distributed to the detector units. This is generally given to a large degree when using a small-surface filament source according to the invention. Moreover, the distribution of the light should be essentially evenly distributed and without a strong spatial dependency, since otherwise the detected light components originate from different light paths. Accordingly, the source and path interferences act on the received light signals in the same way and can be compensated when determining the measured quantity.

In the context of the present invention, a lattice that acts in a spectrally neutral manner is understood to be an evenly distributed, finely divided structure of an optical component in the beam path that deflects the direction of the incoming light in two or more directions toward corresponding detector units. By means of this finely divided structure that is evenly distributed within the receiving aperture of the optical component, there is a diversified distribution of the light toward the detector units. This causes the light bundle to be divided into many small sub-bundles that are then distributed to the detectors and detected there in a bundled manner. Interferences, whose spatial extent is greater than that of a sub-bundle, act on several sub-bundles, and therefore stochastically in the same way on the several detector units, and can be compensated in this way. In contrast, in extreme cases, smaller interferences act selectively on only one detector path. The signal component of an individual sub-bundle which is affected by this and the small interference that is contained therein is however very small in comparison to the overall signal so that the error in the measuring signal that arises in this way can be neglected.

The structure of such a lattice should be as small as possible relative to the entrance surface of the overall light bundle, i.e., the light spot, so that the intensity component of a single sub-bundle relative to the incident overall intensity is as small as possible. On the other hand, the structure should be large enough so that wavelength-dependent diffraction effects do not dominate the light distribution. Given a wavelength in the middle infrared range of between 4 and 5 µm usefully results in a lattice constant of between 20 and 300 µm, preferably 200 µm or less, more preferably 80 µm or less. The lower limit is about 20 µm so that the diffraction effects are not too large. In addition, the deflection angle should not lie within the range of the diffraction maximum of the wavelengths used. For effective interference suppression, the surface components from the several directions should be essentially the same size, and the light intensities should therefore be evenly distributed to the several resulting light paths. The cross-sectional area of the sub-bundles should have the same size so that interferences acting in the beam path impact the sub-bundles in the same manner and can therefore be compensated completely.

A corresponding spectrally neutral lattice can be designed as a reflection lattice. In this case, the light is distributed and additionally deflected, for example by 90°. This facilitates a very complex sensor design. The lattice can exist in a two-dimensional or three-dimensional form that continuously expands in the third direction in space, for example in the shape of a sawtooth structure, in the shape of a gabled roof structure, or more complex shapes such as a pyramidal structure. Two or more directions of light distribution are thereby possible. In this manner, a good spatial distribution and separation of the light to two, three or more detectors can be achieved. By an additional curvature of the entire lattice, such as in the form of a paraboloid, the focus of the incident light on the receiver can simultaneously be moved without additional optical components being necessary for this, such as concave mirrors on the receivers.

Alternatively, the lattice can be a transmission lattice that is formed on or in a transparent material, in particular glass, which is transparent within the wavelength range of the measurement, in particular within the IR range. In contrast to the reflection lattice, a refractive index difference of the substrate to the surroundings, or respectively within the substrate, causes a change and distribution of the direction of the incident light. In this case as well, it is recommendable to use two-dimensional or three-dimensional structures that provide additional focusing.

The combination of the lattice structure with focusing elements or structures is characterized by easy positioning of the optical components in the beam path during sensor production. In particular, this relates to the transmission assembly.

For use within the aforementioned middle infrared range, a slant angle of a reflection lattice of, for example, approximately 27° is useful that achieves an angle between the detectors of about 100° with an exact deflection of 90° without causing light components to be blocked by the lattice itself. By this spreading of the resulting light beams by about 100°, it is possible to position the detector units in the proximity of the lattice, realizing a very compact structure. The deflection of the light striking the lattice by precisely 90° is useful for adjusting and positioning the detector units, and therefore for production.

Preferably, the measuring cell is designed as tubes that are diffuse or have a high-gloss reflection inside, on one end of which the micro-incandescent lamp is arranged, and on the other end of which the sensor or sensors with the upstream bandpass filters are arranged. This facilitates complete transmission of the emitted light and thereby increases the measuring precision. A diffuse reflection, for example by microstructuring the reflective surface, causes an at least partial decoupling of the light incoming to the receivers from the site of origin and hence reduces systematic errors. A high-gloss reflection has the advantage of less light intensity loss. Gold is an exemplary, suitable material for internal mirroring that has good reflection in the IR range and is hardly subject to corrosion due to its nature as a precious metal.

In an advantageous development of the assembly, the at least one bandpass filter is designed as a double bandpass filter that lets IR light pass through both in the measuring wavelength range as well as in the reference wavelength range, wherein the double bandpass filter is upstream from an individual sensor, wherein the control apparatus is designed and configured to modulate the micro-incandescent lamp between an operating point with a lower output and an operating point with a higher output in which the respective emission spectrum has different component ratios in the measuring wavelength range and in the reference wavelength range.

This double bandpass assembly is based on the principle that the filter ranges for gas absorption and the reference wavelengths are combined in an optical double bandpass filter. The light is blocked in all of the ranges except for the two passthrough regions or bands for gas absorption and the reference wavelength. This filter is located in the optical path between the light source and the receiver. The preferably power-regulated quasi-punctiform light source is alternatingly operated at an operating point with lower power, or respectively lower temperature, and an operating point with higher power. At the operating point with lower power, the emission spectrum especially crosses the range of gas absorption. At the operating point with higher power, light passes through both filter ranges to the receiver. The detected light is accordingly dominated by the absorption of the target gas at one point in time, and an additional component is contained at the next point in time that includes the light transmission through the cell. This therefore includes the reference measurement. If the change in the gas concentration within this time interval is negligibly small, the concentration of the target quantity can be determined using the measured values at the points in time of a high and low temperature, or respectively power. In this case broadband transmission changes of the optical path are suppressed like in a two-detector assembly, or by another absorber. Only one receiver is necessary in this assembly.

The signal processing and evaluation for this instance will be briefly described below. For a simplified description, it is assumed that the light component of the reference range is negligible at the first operating point. The following then applies for the light intensity $I_{AP1}$ arriving at the detector at operating point 1 (AP1):

$$I_{AP1} = k_S I_{01} e^{-\alpha xc}, \tag{1}$$

where $k_S$ is a spectrally independent damping factor that depicts interference and constants which describe the amplification, the optical imaging in the system and other influences, for example. The factor $\alpha$ in the exponent designates the wavelength-dependent absorption coefficient of the measuring gas. The terms x and c describe the measuring path in the measuring cell and the concentration of the measuring gas.

At the second operating point (AP2), the light intensity $I_{AP2}$ arriving at the detector is:

$$I_{AP2} = k_S I_{01}(k_a e^{-\alpha x c} + k_b). \quad (2)$$

In this case, the factors $k_a$, $k_b$ include the change in the light intensity from the source in the filter range of the absorption signal at the transition from operating point 1 to operating point 2, or respectively the relationship of the light intensity from the source in the filter range of the absorption signal at operating point 1 to the light intensity from the source in the filter range of the reference signal at operating point 2. These factors thus also include the change in the intensity of the light source in the two windows at the transition from operating point 1 to operating point 2. A conversion results for the concentration, or respectively the target quantity c:

$$c = k_S I_{01} \left( \frac{\frac{I_{AP2}}{I_{AP1}} - k_a}{k_b} \right) \frac{1}{-\alpha x}. \quad (3)$$

This measuring result strongly depends on the proportions of the intensities of the light source at operating point 1 and at operating point 2. The practical evaluation is preferably carried out using calibrated curves or lookup tables since $k_a$, $k_b$ cannot be determined in a practical system during runtime.

The double bandpass filter assembly only requires one optical channel and one detector unit, resulting in a robust and optically simple design that offers strong protection against optical interferences, changes in amplification and the sensitivity of the receiver. The optical power provided is not distributed to several receivers. The quasi-punctiform light source can be precisely modulated by optical or purely electronic power regulation which makes referencing, or respectively reference measurement, highly stable. The operating points can be checked by using the time characteristic of the detected signal during modulation. Additional advantages of this assembly are the low power consumption due to the use of only one reception channel, and the low production costs due to the low number of optical and electronic components.

In another advantageous development of the aforementioned assemblies, means are included that are configured for temporarily increasing the pressure and/or reducing the pressure of the gas mixture in the measuring cell, in particular a pump and/or one or more in particular switchable valves. Such valves can be switchable valves or other valves such as check valves or pressure relief valves. Preferably, a control apparatus is included that is configured to control the means for temporarily blocking a gas outlet of the measuring cell, and/or to increase and/or lower the amount of the gas mixture to be analyzed in the measuring cell. Alternatively, the pressure variation can also be used with the assistance of an external device in addition to the actual sensor module.

This measure advantageously represents a supplement to sensors based on conventional side stream measuring assemblies for sensor calibration, which is recommendable for longer intervals in time. A significant pressure change is used for referencing, for example from a large increase in pressure, or a variation of the pressure from an underpressure to an overpressure in the measuring cell. To generate an overpressure, a pump can be used for example in combination with a check valve in front of the measuring cell, wherein the flow direction is changed, and the pump that otherwise draws gas out of the measuring cell causes the gas to be compressed in the measuring cell. It may be economically sensible to use an external device that includes the necessary hardware for performing the pressure manipulation. Such an additional device is advantageously connected to the pneumatic inputs and outputs of the measuring cell. If the sensor system, or respectively the assembly, is designed for such an external calibration, the raw data can be tapped, calibration data can be acquired, and updated calibration parameters can be transmitted to the sensor. In this way it is possible to economically design cyclically required calibration without expensive calibration gases.

This measure primarily occurs in a side stream since the gas mixture drawn into the side stream can be built up and manipulated in terms of pressure comparatively easily. A nonlinearity of the absorption of the target quantity that goes beyond the law of absorption is thus used in order to separate it from weaker and especially broadband background absorptions and thereby enable a selective and robust measurement of the target substance. An intensity drift of the source and changes in the transmission of the transmission path are also suppressed in this method with respect to the target quantity. Since building up the measuring gas means an interruption in the actual measurement, it is a cyclical method. It can be combined with continuous single channel measurement as well as with multichannel measurement in order to effectively compensate inter alia for interfering effects.

The nonlinearity measurement is not limited to the application of absorption measurement with small-volume IR light sources. In the present case, it can be added to a previously described continuous measurement of a target quantity and determination of concentration. The determination of the nonlinearity requires several measurements to be made over the time period of the buildup in pressure, or respectively the change in pressure so that the nonlinearity can be deduced from the relationship between the measured values and development in pressure. To accomplish this, in the context of the nonlinearity measurement, the flow of the measuring gas is briefly blocked cyclically, preferably when there is a high concentration of the target quantity such as expiratory $CO_2$. For this, drawing the gas to be measured can for example be stopped for a short time by for example reversing the flow direction of a pump, wherein the pump operates against a valve, in particular a check valve, in front of the measuring cell and thereby compresses the gas mixture in the cell. If applicable, reducing the pressure is analogously possible by throttling the valve before the measuring cell and retaining the direction of flow of the pump. In this manner, the transmission of the assembly at different pressures of the gas in the measuring cell is detected. If a significant change in pressure is reached in the cell, the pump restarts suctioning and continuous measurement restarts.

The change in pressure does not influence the light source, the light transmission and the receiver. These quantities can be assumed to be constant over the duration of the change in pressure. Significant changes, drift phenomena, aging effects, etc. have a greater time constant than the duration of the change in pressure and nonlinearity measurement. In contrast to optical and electronic transmission, the absorption changes in the measuring cell with the pressure, however. Since the pressure of the gas in the measuring cell is also measured, the unknown transmission data of the measuring path can be determined in this way.

By suitably designing the optical filter, the strength of the nonlinearity of the absorption of the target quantity can be influenced in conjunction with the optical gas absorption of the target quantity. Such a nonlinearity of the absorption does not occur in other overlapping, broadband absorbers that are generally weaker and also may be included in the gas mixture. By using this property, the target quantity can also be selectively determined without using an additional reference wavelength measurement. The concentration value of the target quantity ascertained in this way can be used to correct the values between the pressure cycles.

Physically, the nonlinearity results from the overlapping of the wavelength-dependent transmission characteristic of the filter with the wavelength-dependent absorption coefficient of the measuring gas that underlies the transmission of the light through the measuring cell and the gas to be measured within the wavelength range of the optical filter and the absorption of the measuring gas. If the transmission window of the filter includes the tails of the absorption bands of the measuring gas, the absorption of the light passing through increases nonlinearly with the increase in the concentration when the concentration of the measuring gas is increased in the measuring cell. This is an effect that exclusively results from the measuring gas to the extent that other gases in the gas mixture and other effects of the measuring apparatus cause an attenuation of the light that is largely independent of the wavelength within the corresponding spectral window of the filter. Only one transmission channel from a light source to a detector unit is required, wherein a "detector unit" is to be understood as a detector and possibly an optical filter. The light from the source should be amplitude modulated since constant components must be suppressed. In the following, the alternating signal amplitudes will be considered. The detected light power on the detector surface, or respectively the light intensity $I_M$ received by the detector can be described as:

$$I_M = I_0 k_S T_{ges}, \quad (4)$$

wherein $I_0$ is the light intensity emitted by the light source, $k_S$ is a spectrally independent damping factor that includes interferences and constants that describe the amplification, imaging, etc. in the system, for example, and $T_{Total}$ describes the wavelength-dependent transmission of the overall system. This factor is a product $$T_{total} = T_G T_S T_F \quad (5)$$

of the wavelength-dependent and pressure-dependent transmission $T_G$ of the target gas, the wavelength-independent and pressure-dependent transmission $T_S$ of interfering gases, as well as the pressure-independent and wavelength dependent transmission $T_F$ of the optical system from the optical filter, spectral sensitivity of the detector, the spectral characteristic of the emission source as well as the transmission properties of the cell. For the method, it is important that the transmission range of the bandpass filter is not just matched with the maximum of an absorption length of the target gas in a very narrow band, but that ranges with low absorption are also included. Moreover, the filter passthrough band should be selected so that interfering gases have an essentially constant absorption characteristic in this region. Moreover, the filter bandwidth should be kept narrow taking into account the stated considerations so that spectral, or respectively dispersive, e.g., temperature-dependent, changes of the generally broadband light sources and detector have little to no effect on the measuring results.

Taking into account the pressure dependency and wavelength dependency equation (4) can be described as a sum of the n spectral components:

$$I_M(p) = \frac{I_0}{n} k_S T_S(p) \sum_n T_{Gn}(p) T_{Fn}. \quad (6)$$

After applying the law of absorption and taking into account the pressure dependency of the particle density in the measuring gas, the following results:

$$I_M(p) = \frac{I_0}{n} k_S e^{-\alpha_s x c_S \frac{p}{p_0}} \sum_n e^{-\alpha_{Gn} x c_G \frac{p}{p_0}} k_{Fn}, \quad (7)$$

and expressing formula (7) as a logarithm:

$$\ln I_M(p) = \ln\left(\frac{I_0}{n} k_S\right) - \alpha_s x c_S \frac{p}{p_0} + \ln\left(\sum_n e^{-\alpha_{Gn} x c_G \frac{p}{p_0}} k_{Fn}\right), \quad (8)$$

The logarithm of the measuring signal can thus be expressed as the sum of three terms of which one is pressure-independent, one is linearly dependent on pressure, and a third contains a component that is nonlinearly dependent on pressure. The linearly dependent component contains the interfering gas absorption, and the nonlinear component contains the target gas information. By means of further signal processing, these components can be separated from each other, thereby eliminating interfering influences in the measuring signal.

This can for example be accomplished by using the pressure derivative of function (8), whereby the pressure-independent signal components are removed from the measuring signal, and the nonlinear component resulting from the target gas remains as the only pressure-dependent component. Given the linearity of the pressure dependency of the potential interfering gas component, a constant value remains after the derivation:

$$\frac{d}{dp} \ln I_M(p) = -\frac{\alpha_s x c_S}{p_0} + \frac{d}{dp} \ln\left(\sum_n e^{-\alpha_{Gn} x c_G \frac{p}{p_0}} k_{Fn}\right). \quad (9)$$

The interfering gas component thereby forms an offset and can be separated from the signal component of the target gas by considering the difference in the signal at various operating points, or by a second derivation according to pressure. The resulting signal progression is dependent on pressure in a nonlinear manner, although proportional to the concentration of the target gas. The curve characteristic of this nonlinear relationship, which can be advantageously saved as a functional approximation or as a lookup table to calculate the concentration in the signal evaluation, is essentially determined by the absorption curve of the target gas and the chosen transmission characteristic of the optical filter and can therefore be optimized for certain concentration measuring ranges. A series of interfering quantities can be suppressed in this manner although only one measuring path is used in the design. By recursive calculation, the signal component of the interfering gas can then also be calculated, which for example in capnometry provides an approximate indication of the concentration of $N_2O$ as the strongest interfering gas in capnometry.

Thus by using only one measuring path, a determination of concentration is feasible which, apart from the SNR, is independent from the wavelength-stable transmission of light intensity from the source to the detector within the optical filter bandwidth. This dispenses with a few sources of error that for example arise from aging. A zero reference measurement, such as a cyclical measurement of ambient air is unnecessary in this method. Instead, the absolute concentration can be determined. Given the simple optical design, high light transmission with very low loss and consequently very good SNR is possible. Other broadband influences relative to the filter bandwidth such as other absorbers are effectively suppressed. Correspondingly, the assembly is more robust against spectral fluctuations in the emission from the source and the sensitivity of the detector in comparison to methods with two or more separate wavelength ranges for measuring gas absorption and the spectral reference. This is because only the bandwidth of the filter in the absorption band is effective while referencing, and not the spectral distance between the absorption filter range and the reference range. This method can be integrated to compensate for potential drift effects in combination with existing side stream methods.

A different parameter from the aforementioned formulas can be intentionally changed in an analogous manner instead of modulating the pressure in the measuring cell, and the change of the measurement with respect to its nonlinearity can be used. This applies for example to the absorption coefficient $\alpha$, the absorption length x or the concentration c.

Likewise, the underlying object of the invention is achieved with a method for measuring a gas concentration by means of absorption spectroscopy, in particular for the capnometric measurement of the proportion of $CO_2$ in breathing air in an above-described assembly according to the invention, in which IR light is guided from a thermal light source through a measuring cell with a gas mixture to be analyzed, and the gas concentration of a gas to be measured that is contained in the gas mixture is determined by measuring an attenuation of the light introduced into the measuring cell caused by absorption by the gas to be measured, wherein the method is further developed in that the thermal light source is designed as an encapsulated micro-incandescent lamp with a light-generating coil, wherein in particular a sensor or several sensors are designed as infrared-sensitive photodiodes with a sensitive surface that is less than 1 $mm^2$, in particular less than 0.15 $mm^2$.

The method according to the invention accordingly achieves the same advantages, features and properties as the invention according to the above described assembly. The method as well as the assembly can advantageously be used both in the side stream method as well as in the main stream method.

Preferably, the thermal light source is modulated with a measurement repetition frequency $f_{Mess}$ that is greater than 10 Hz, in particular greater than 25 Hz, wherein a temperature of the coil is greater than 400° C. during measurement, and has a temperature modulation rise of at least 300° C., in particular at least 500° C., in particular exceeds 1000° C. at a maximum. The measurement repetition rate ensures that the progression of the $CO_2$ concentration in the breathing air is sampled sufficiently even in the event of a fast respiratory rate. High respiratory rates occur in medical emergencies as well as in neonatal medicine, i.e., in newborns and premature babies.

The use of high temperatures of the thermal light source ensures that there is sufficient intensity at a wavelength of about 4.26 μm, i.e., within the absorption band of $CO_2$. At a maximum, the temperature is however significantly higher than is routine in capnometry, and significantly higher intensities are therefore available at the measuring wavelengths. This is facilitated by selecting a quasi-punctiform filament source that can be encapsulated in a thin glass housing without a significant loss of light intensity.

The micro-incandescent lamp is preferably operated with power control. In this manner, very precise and reproducible controlling of the light intensity and the emitted spectrum of the light corresponding to the temperature of the spiral-wound filament can be realized, especially with the quasi-punctiform filament sources of the present invention which exist in micro-incandescent lamps. Since the very small spiral-wound filament has a very small thermal mass, hysteresis effects such as a temperature lag relative to the variably supplied power are acceptable, even with the required modulation frequencies. Furthermore, given the small thermal mass, a comparatively fast control and change in temperature of the spiral-wound filament is possible.

An efficient type of quasi-continuous suppression of interference and determination of the concentration results when, over the course of measuring, the gas mixture pressure in the measuring cell is increased and/or lowered sequentially over intervals in time and the absorption is measured depending on the pressure, wherein to change the pressure, in particular, an outflow of the gas mixture is interrupted, and/or an inflow or an outflow of the gas mixture is supported and increased by a pump. The dependency of the absorption in the gas mixture is non-linear due to the tuning of the bandpass that lets through the absorption range of the gas to be measured to the absorption band of the gas to be measured. This non-linearity of the pressure dependency of the absorption in the measuring cell is used to isolate the input of the amount of the gas to be measured from other inputs that do not yield a corresponding nonlinear input. The nonlinearity of the pressure dependency of the measured absorption therefore offers an independent reference of the absorption measurement.

A method having its own inventive value that can also be used in the context, but not just in the context, of the above-described assembly according to the invention and the above-described method according to the invention relates to a method for measuring a gas concentration by means of absorption spectroscopy, in particular for the capnometric measurement of the proportion of $CO_2$ in breathing air, in particular according to one of the above-described methods according to the invention, in particular in an above-described assembly according to the invention, in which light, in particular IR light, is conducted from a light source, in particular a thermal light source, through a measuring cell with a gas mixture to be analyzed, and the gas concentrations of a gas to be measured that is contained in the gas mixture is determined by measuring an attenuation of the light introduced into the measuring cell caused by absorption by the gas to be measured, characterized in that over the course of measuring, the gas mixture pressure in the measuring cell is, at intervals in time, increased and/or lowered, or fluctuations in the gas mixture pressure are measured, and the absorption is measured depending on the pressure, wherein a pressure-dependent measuring series is analyzed with respect to components that are linearly and nonlinearly dependent on the pressure, and in particular the component that is nonlinearly dependent on the pressure is used to measure the gas concentration of the gas to be measured, or to correct and/or calibrate a measurement of the gas concentration of the gas to be measured.

The fundamentals of this nonlinearity measurement that can alternatively also be based on intentional changes in the absorption constant or the absorption length have been described above in conjunction with the assembly using the above-cited formulas (4) to (9). This nonlinearity measurement can also be applied to gas absorption measurements within visible light or other wavelength ranges in addition to the above-described context as long as the target gas has a narrow absorption band on which an optical bandpass filter is placed in comparison to interfering influences.

Further features of the invention will become apparent from the description of embodiments according to the invention together with the claims and the attached drawings. Embodiments according to the invention can fulfill individual features or a combination of several features.

BRIEF DESCRIPTION OF THE DRAWINGS

The invention is described below, without restricting the general idea of the invention, based on exemplary embodiments in reference to the drawings, whereby we expressly refer to the drawings with regard to the disclosure of all details according to the invention that are not explained in greater detail in the text. In the following.

In the drawings, the same or similar elements and/or parts are always provided with the same reference numbers; a reintroduction will therefore always be omitted.

DETAILED DESCRIPTION

Figure 1:
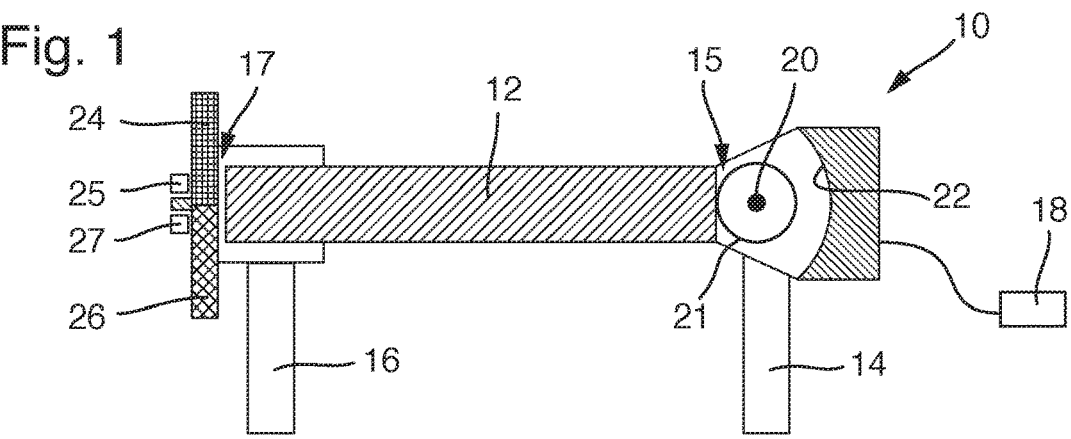
FIG. 1 shows a schematic depiction of a first exemplary embodiment of an apparatus according to the invention for the side stream, FIG. 2 a)-c) show schematic diagrams of beam paths for capnometry FIG. 3 a), b) show schematic depictions of apparatuses according to the invention with optically neutral transmission lattices, FIG. 4 a)-f) show schematic depictions of optically neutral reflection lattices that can be used according to the invention.

In FIG. 1, a first exemplary embodiment is schematically depicted of an assembly 10 according to the invention for the side stream. It can be a capnometer that comprises a measuring cell 12 which is supplied through a gas inlet 14 and a gas outlet 16 with a constant flow of breathing air by a pump (not depicted) that has been branched from a main flow of breathing gas of a patient. For this, the measuring cell 12 also has a gas inlet opening 15 and a gas outlet opening 17 on its opposing side. The gas outlet opening 17 is preferably arranged entirely around the measuring cell 12 so that the required cross-section of the gas outlet can be realized with a minimum distance between the measuring cell and filter. The measuring cell 12 is designed cylindrical with a diameter that is small relative to the length of the measuring cell 12. Accordingly, the volume of the measuring cell 12 is minimized relative to the available absorption length, i.e., the length of the measuring cell 12. Minimizing the volume has the advantage that the measuring gas only has a short retention time in the measuring cell 12, and therefore enables very precise, high-resolution measurement over time of the concentration of a target gas in the measuring gas.

For measurement, the assembly 10 comprises a quasi-punctiform filament source in the form of a micro-incandescent lamp 20 that is arranged in an evacuated glass bulb. This makes it possible for the light source to shine at a very high power and very high temperature without negatively influencing its service life. The main portion of the emitted light lies in the infrared range for capnometry, in particular in the middle infrared range. The micro-incandescent lamp 20 lies within the focal point of a spherical or parabolic reflector 22 that renders the light beams largely parallel so that the light shines through the measuring cell 12 as evenly as possible. The measuring cell 12 can be reflective on the inside.

An assembly consisting of two detectors 25, 27 with two upstream filters, 24, 26 and that are illuminated as evenly as possible by the light that shines through the measuring cell 12 is located at the output of the measuring cell 12. A filter 24 for a gas channel is located upstream of the detector 25 and has a narrow bandpass for the absorption bands of the target gas, whereas the filter 26 is designed as a bandpass filter for a reference channel where the target gas has no or only slight absorption. A control and evaluation unit is not depicted. The use of a quasi-punctiform light source in the form of a micro-incandescent lamp 20 makes it possible in this case to realize very high measuring precision with very little light loss, and also to achieve very fast and precise power and temperature control of the light source.

Likewise, an evaluation apparatus 18 is symbolically depicted that receives signals from the detectors 25, 27 and ascertains the concentration of the target gas in the measuring cell 12 according to internal calculation rules, look-up tables, etc. and a corresponding calibration.

Figure 2:
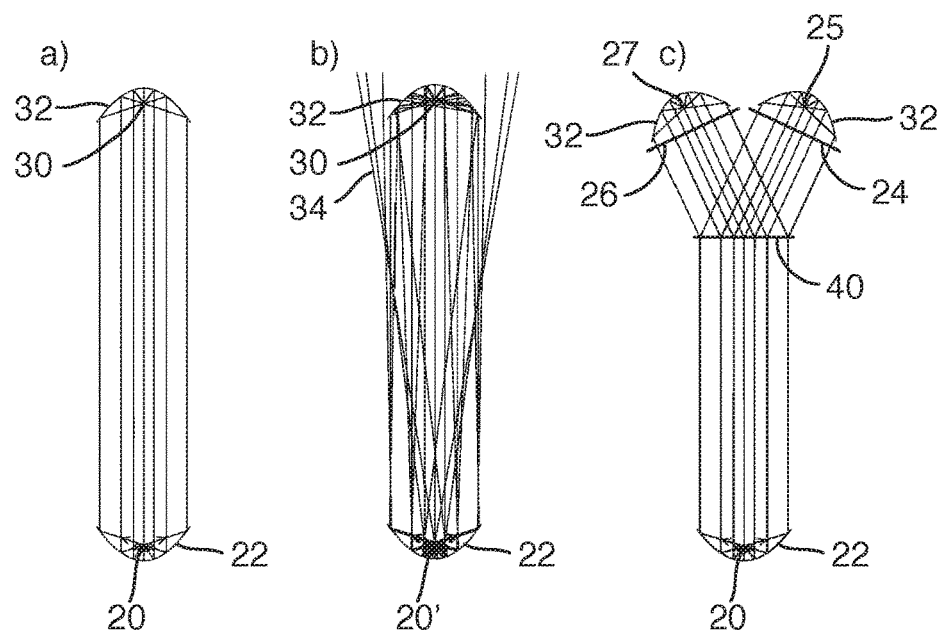

For the sake of illustration, FIG. 2 a)-c) depict schematic diagrams of beam paths for capnometry. FIG. 2 a) shows the basic shape of a channel in which a quasi-punctiform infrared light source, in particular a micro-incandescent lamp 20, is arranged in the focal point of a parabolic reflector 22 that renders light beams emitted from the focal point of the reflector 22 a parallel light beam bundle. This parallel light beam bundle is in turn focused by a reflector 32, which is also designed as a parabolic reflector, onto the focal point of the reflector 32 in which a sensor 30 is arranged, which preferably also has a small volume, such as a photodiode. Only very little light is lost in this light transmission so that a good signal-to-noise ratio (SNR) can be achieved with a relatively low initial intensity.

In contrast to this, the instance is depicted in FIG. 2 b) in which the light source 20' is not quasi-punctiform. In this case, part of the light source 20' lies outside of the focal point of the reflector 22 so that the emitted light is not entirely transmitted as a parallel light bundle to the opposing reflector 32, but rather passes the reflector 32 in a nonparallel manner and is accordingly lost. Because of this light loss, the amount and intensity of emitted light must be greater than in the instance according to the invention, which leads to inefficiency and greater power consumption.

FIG. 2 c) shows another example in which the light is also generated in the same way as depicted in FIG. 2 a), however the parallel light bundle contacts a schematically depicted, spectrally neutral transmission lattice 40 that divides the light bundle without dispersive effects, i.e., spectrally neutral, into two different light bundles which are distributed by the corresponding filters 24, 26 for a gas channel and a reference channel 20 to two corresponding reflectors 32 and the corresponding sensors 25, 27 for a gas channel and a reference channel.

Figure 3:
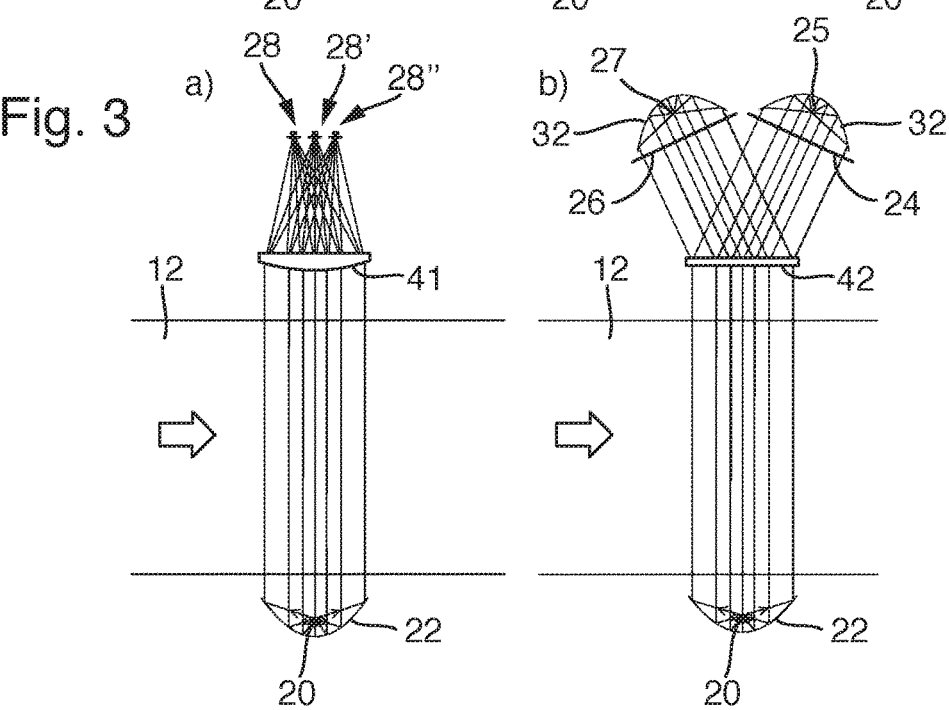

FIG. 3 a), b) show schematic depictions of the optical conditions of apparatuses according to the invention with spectrally neutral transmission lattices. FIG. 3 a) shows an instance in which the light is generated as in FIGS. 2 a) and 2 c). After passing through the measuring cell 12, the parallel light bundle reaches a spectrally neutral transmission lattice 41 that also focuses by means of a corresponding curvature. In the shown embodiment, the parallel light bundle comes to be by focusing the spectrally neutral transmission lattice 41 on three different small-surface sensors 28, 28', 28" that for example can be designed for one reference channel and two different target gases with different absorption ranges, alternatively also for three different target gases, or also for one gas and two reference wavelengths which then enables dispersion compensation.

In the portrayed case, the light passes through the measuring cell 12 perpendicular to the direction of flow of the gas mixture. This can be used both in a main stream as well as in a side stream. For use in a side stream, the coupling into, and respectively out of, the measuring cell 12 can however also be configured to be collinear with the main stream direction in the measuring cell 12.

Figure 4:
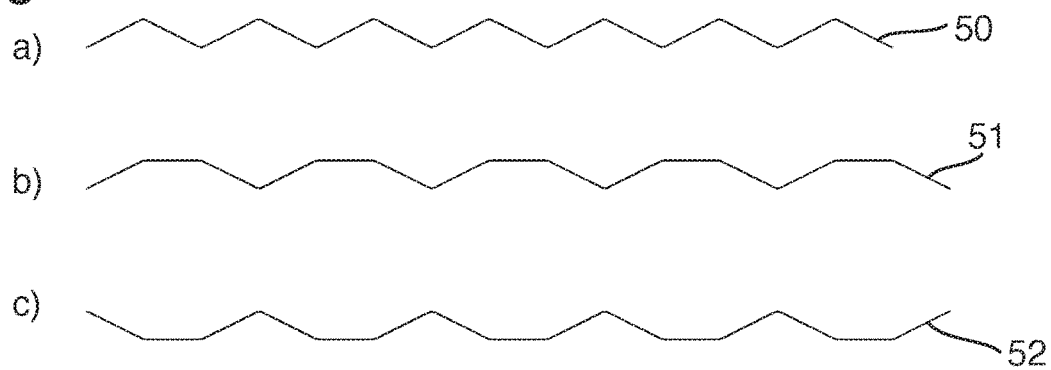

FIG. 4 a)-f) show schematic depictions of spectrally neutral reflection lattices that can be used according to the invention. The structure 50 from FIG. 4 a) shown in a cross-section serves to distribute the light to two detectors; the structures 51, 52 from FIGS. 4 b) and 4 c) serve to split the light toward three detectors. FIG. 4 d) shows a three-dimensional, specific depiction of a reflection lattice 53 that, by its gable roof structure, serves to distribute to two detectors similar to the structure 50 from FIG. 4 a). FIG. 4 e) shows a perspective depiction, and FIG. 4 f) shows a front, plan view of a surface structure of a reflection lattice 54 that is based on a pyramid structure with a hexagonal basic structure. This reflective lattice 54 is suitable for distributing the light to six detectors.

Figure 5:
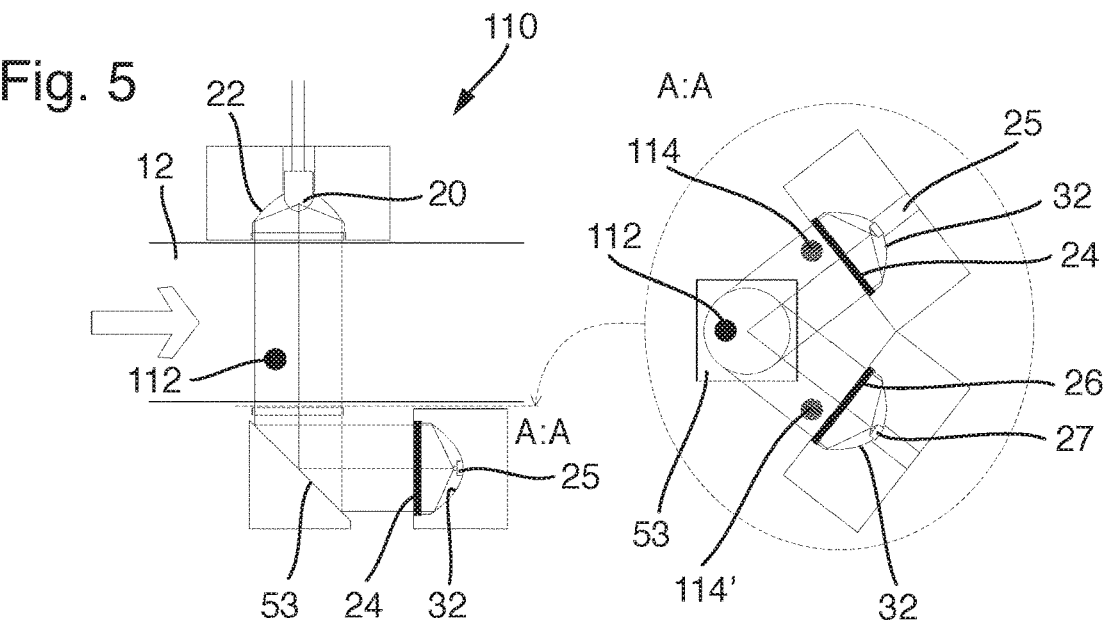
FIG. 5 shows a schematic depiction of a second exemplary embodiment of an apparatus according to the invention.

FIG. 5 shows a schematic depiction of a second exemplary embodiment of an assembly 110 according to the invention with a left partial image in a side view and with a right part in a frontal plan view following plane A:A from the left partial image. The micro-incandescent lamp 20 is enclosed in a holder that has a parabolic reflector 22 which converts the emitted light into a parallel beam bundle and shines through the measuring cell 12 of the assembly 110 through which measuring gas flows from the left (in the direction of the arrow). This assembly therefore corresponds more to a measurement in a main flow; however, it can also be suitably used for a side stream measurement, or can be optimized for a side stream measurement by correspondingly coupling the light in and out in the measuring cell 12.

After exiting the measuring cell 12, the light bundle is deflected 90° in the shown view by a reflection lattice 53 corresponding to FIG. 4 b), wherein in this case a group consisting of a filter 24 for the gas channel and a detector 25 for the gas channel of the target gas is depicted as the detector unit, wherein the small-surface detector 25 is arranged in the focal point of the parabolic reflector 32. To protect the individual components, three additional unidentified, optically transparent and spectrally neutral entry and exit windows are also depicted.

In the right depiction in FIG. 5, it is discernible how the reflection lattice 53 divides the light bundle drawn as a circle into two different light bundles for two equivalently designed detector units for the absorption channel and the reference channel. The reference numbers correspond to those from FIG. 2 c) and FIG. 3 b).

An advantage of this design in the event of contaminants in the optical path is also shown in FIG. 5. Interference 112 is formed in the measuring cell, for example a drop of condensation or a dirt particle that is arranged fixed or movable in the measuring cell 12. The reflection lattice 53 ensures that this interference is similarly in both channels, i.e., in the absorption channel and the reference channel, ensuring that such interference does not impair measurement. This can be seen in the right depiction in FIG. 5 where the images 114, 114' of the interference 112 appear in both channels in the same manner and cause an attenuation of the signal in the same manner. Since the concentration is measured by the absorption, i.e., the comparison of intensities in the absorption channel and in the reference channel with each other, both channels are affected in the same way. The structure of the images 114, 114' is a result of distributing all the light to both detectors 25, 27 by the gable roof structure of the reflection a lattice 53. Since both channels are affected, this input substantially cancels itself out without substantially impairing the relationship between the measured intensities.

Figure 6:
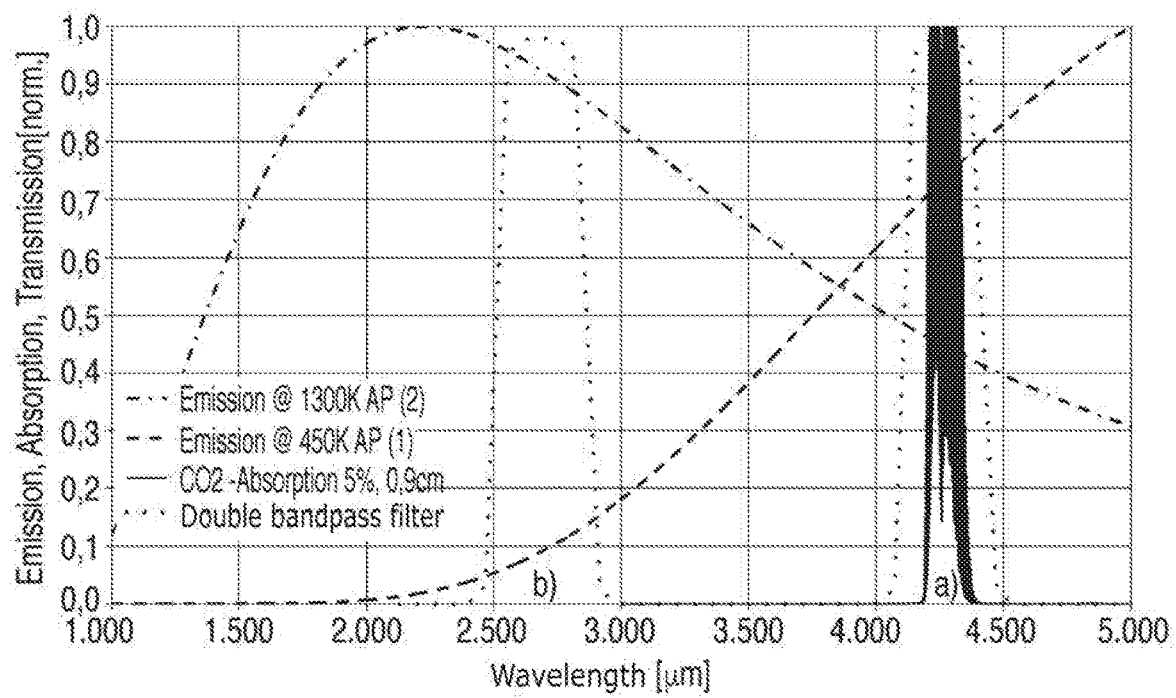
FIG. 6 shows spectral characteristics of two operating points of a light source as well as a filter and absorption characteristic for a capnometry application.

FIG. 6 shows spectral characteristics of a light source at two operating points as well as a filter and absorption characteristic for a capnometry application. The wavelength is depicted on the horizontal axis within a range of 1 to 5 µm, i.e., the infrared range; on the vertical axis, normalized values are depicted for the emission, absorption and transmission between 0 and 1. According to the legend at the bottom left, the $CO_2$ absorption of a 5% concentration and an absorption length of 0.9 cm at about 4.26 µm are portrayed as a solid line. A range a) of a double bandpass filter is drawn around this absorption band that lets infrared light within a range of about 4.1 to 4.4 µm pass through so that the entire range that is absorbed in $CO_2$ falls within this range a) of the double bandpass filter. A second range b) of the double bandpass filter serves as a reference filter that lets infrared light pass through approximately between 2.5 and 2.8 µm. Here, $CO_2$ does not possess any absorption.

The emission of a thermal emitter is depicted by a dot-dashed line and a dashed line at a first and second operating point (AP) at 1300 K and 450 K, respectively. At the higher temperature, the maximum of the light intensity is at about 2.25 µm, whereas the portrayed characteristic has not yet reached its maximum with a thermal emitter temperature of 450 K. It should be noted that the emitted power is also greater at a higher temperature so that the two emission spectra in the depiction in FIG. 6 have very different scaling factors from each other.

It is clearly discernible that at the lower temperature at operating point 1, there is very little light intensity in reference band b), although there is much more intensity in absorption band a). At a higher operating point 2 at 1300 K, the light intensity in the reference band b) is however higher than in the absorption band a) so that, given a knowledge of the respective emission spectrum, a clear distinction between the components of the reference and the gas absorption can be made by means of a corresponding temperature modulation. This can be very precisely adjusted within the framework of a calibration.

Figure 7:
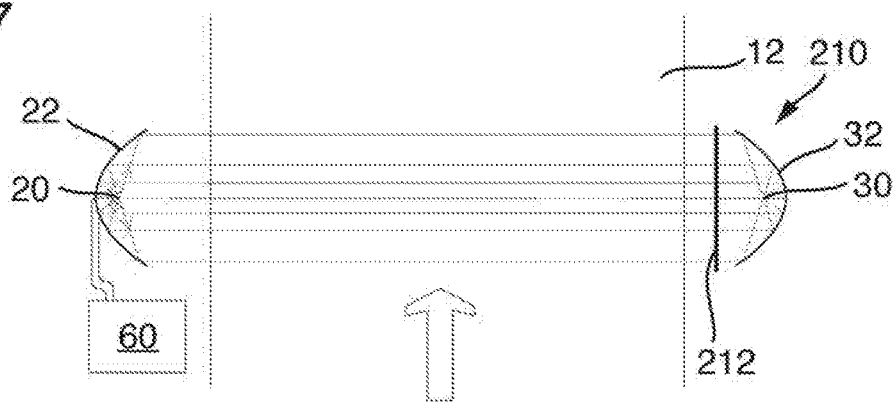
FIG. 7 shows a schematic depiction of a third exemplary embodiment of an apparatus according to the invention, FIG. 8 a), b) shows schematic depictions of power control circuits that can be used according to the invention.

FIG. 7 shows a schematic depiction of a third exemplary embodiment of an assembly 210 according to the invention in a double bandpass assembly so that the spectrum conditions from FIG. 6 apply in this case. The optical assembly of one channel with which the measuring cell 12 is irradiated corresponds to the one from FIG. 2 a). This assembly can also be used in a main stream or in a side stream and, by suitably coupling in and coupling out the light in the measuring cell 12, the light can be guided in the direction of flow the measuring cell.

In the instance shown in FIG. 7, the light emitted by the micro-incandescent lamp 20 is filtered after passing through the measuring cell 12 by a double bandpass filter 212 with the spectral characteristic from FIG. 6 and focused on the individual sensor 30. For this, a control apparatus 60 with a performance control is provided that very precisely controls the power output and temperature of the quasi-punctiform thermal emitter, i.e., the micro-incandescent lamp 20, in order to adjust the corresponding emission spectra from FIG. 6 to modulate very quickly, or suitably select other temperatures with the corresponding emission spectra.

Figure 8:
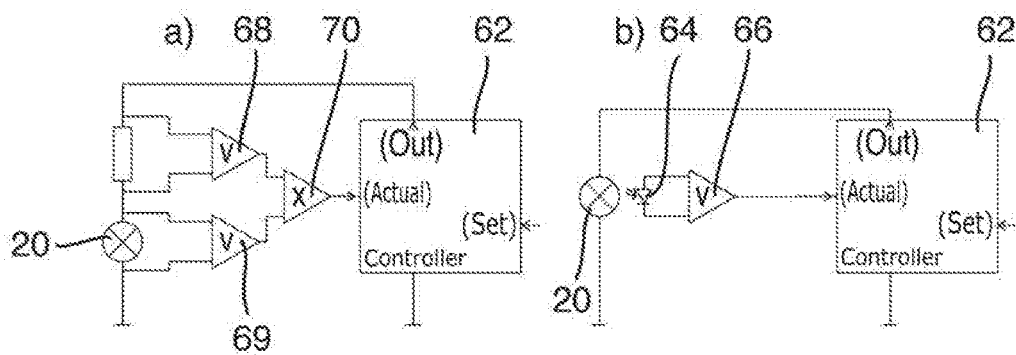

FIG. 8 a), b) schematically depict power control circuits according to the invention that can be used for this. A multiplication circuit is realized in FIG. 8 a) in which a momentary current and a momentary voltage drop over the micro-incandescent lamp 20 are measured by two amplifiers 68, 69, the current and voltage are multiplied with each other in a multiplier 70 and entered into a control unit 62 as an actual value that is compared with a target value, and controls the light source via a series resistor as an output value (Out). The measurement of current and resistance and the multiplication can be either analog or digital.

Alternatively according to FIG. 8 b), the light power emitted by the light source 20 can also be measured by a photodiode 64 whose output current is in turn fed as an actual value via an amplifier 66 to the control unit 62 that then correspondingly regulates the power of the micro-incandescent lamp 20 to the variable target value.

The solution according to FIG. 8 b) is simpler than that from FIG. 8 a), however it should be noted that a section of the spectrum of the light source is used for controlling the light source that does not serve to measure $CO_2$, but is instead proportional thereto. In addition, it is useful to use a shortwave photodiode for control in comparison to the measuring wavelength, for example within the visual spectrum or in the near infrared since this enables much more stable control. These photodiodes normally have a spectrum with a narrower band in comparison to the emission spectrum of the micro-incandescent lamp 20 so that the target values must be correspondingly adapted. If applicable, nonlinearities should also be taken into account that arise from the overlap of the respective temperature-dependent emission spectrum with the sensitivity spectrum of the sensor.

Figure 9:
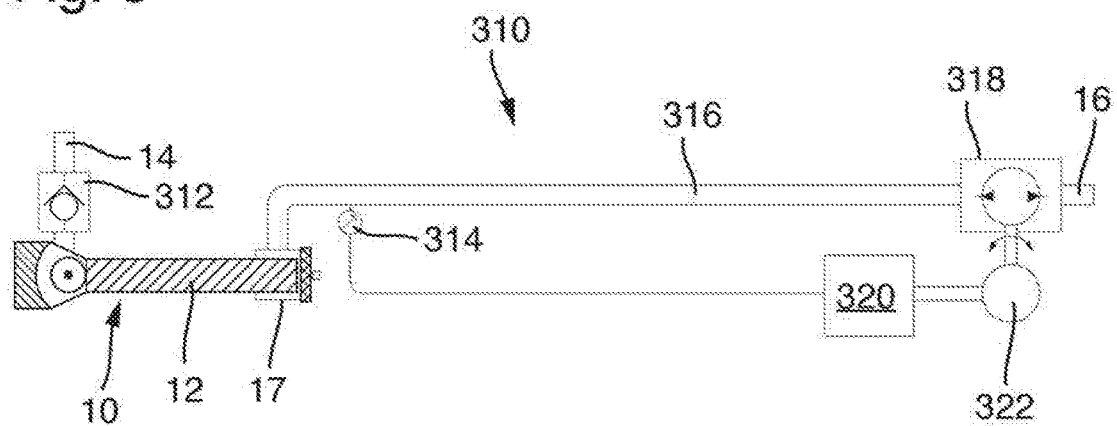
FIG. 9 shows a schematic depiction of a fourth exemplary embodiment of an apparatus according to the invention.

FIG. 9 shows a schematic depiction of a fourth exemplary embodiment of an assembly 310 according to the invention that can be linked to any of the above exemplary embodiments, i.e., to those exemplary embodiments that only have one optical channel as well as to those exemplary embodiments in which the light bundle is divided into two separate optical channels after passing through the measuring cell 12. Merely as an example, an assembly 10 according to the first exemplary embodiment from FIG. 1 has been selected as the basis for the assembly 310. A modification exists in that the gas inlet 14 is equipped with a check valve 312 which opens in the gas inlet direction and blocks against this direction. At the output for the measuring cell 12 and the gas outlet opening 17, a gas outlet 16 is attached that expands to a gas reservoir 316 and is equipped with a pressure gauge 314 to measure the gas pressure in the gas reservoir 316, wherein the measured pressure also corresponds to the pressure in the measuring cell 12.

Furthermore, a pump 318 is provided that can pump gases either into the narrow gas reservoir 316 and the measuring cell 12, or can be operated in the reverse pump direction in order to conduct gas out of the measuring cell 12 and thereby increase the pressure in one pump direction and lower it in the opposite pump direction. To do this, a controller 320 for the pump 318 is provided that controls the pump rotor via a motor 322 that can be designed as an actuator, or directly, and influences the direction and/or the strength of the pump 318. With this arrangement 310, it is possible to perform a nonlinearity analysis depending on the pressure available in the measuring cell 12 as described above, for example according to formulas (8) and (9). Accordingly, it is inter alia possible to achieve a cyclically recurring pressure change in the measuring cell 12 that can be used as an independent analysis in order to check whether the calibration parameters of the underlying continuous measurement are still correct or must be adapted since the concentration of the target gas can be isolated from interfering sources with the assistance of this method. Since this nonlinearity measurement has the best precision at high target gas concentrations, it is preferable to undertake pressure modulation when for example, the end expiration value, typically about 5% $CO_2$, has been reached during expiration.

Figure 10:
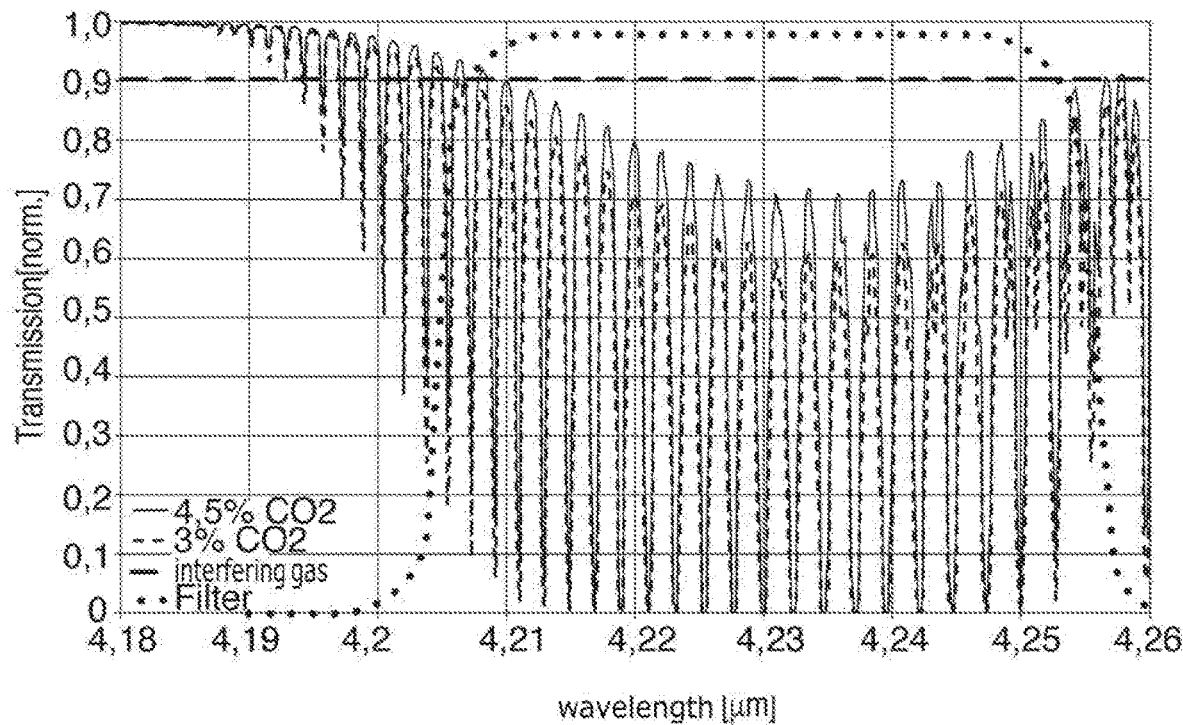
FIG. 10 shows a depiction of high-resolution spectral characteristics of the absorption band of $CO_2$ and a bandpass filter that can be used according to the invention, and FIG. 11 a)-d) show a schematic depiction of a micro-incandescent lamp.

The underlying spectral characteristics for this analysis are depicted in FIG. 10 in high resolution. The wavelength range between 4.18 and 4.26 μm depicted on the horizontal axis corresponds to a narrow section from the spectrum range depicted in FIG. 6. The band structure of $CO_2$ absorption can be clearly seen, in this case a depiction of transmission. In contrast to the double bandpass filter from FIG. 6, a narrower bandpass filter is used in this case that cuts off the edge regions of the absorption of $CO_2$ and is thus comparatively slightly narrower than the $CO_2$ absorption band. A bandwidth that is too small would undesirably reduce the available light intensity; however, very strong nonlinearity in the pressure dependency is ensured with the shown configuration. The intensity arriving at the detector results, from a mathematical perspective, from an overlapping of the filter function with the wavelength-dependent function of the target gas absorption coefficient with its band structure. This overlap causes a nonlinear dependency of the detectable transmission on the pressure, or respectively the concentration of the target gas.

Also drawn is an interfering gas absorption coefficient that is basically assumed to be constant in the depicted range and which also reduces the transmitted light power. Since however the absorption coefficient of the interfering gas is wavelength-independent, the overlapping of the filter function of the interfering gas transmission in this range only yields linear and no non-linear pressure-dependent terms.

FIG. 11 a) schematically depicts a micro-incandescent lamp 20 as an example that can be used according to the invention. This comprises a coil 81 as a central light generating unit which is arranged in a capsule 84 that is evacuated or filled with an inert gas. The area around the coil 81 is provided with a vacuum 85. The capsule 84 itself is transparent, for example made of glass. The evacuated interior is sealed at the bottom by a solid base 87 which is penetrated by two supply conductors 86 that terminate in contact pins 88 which the coil 81 contacts. The capsule 84 has a basically cylindrical shape with a diameter 90 in relation to the longitudinal axis of the micro-incandescent lamp 20. This is advantageously less than 2 mm, wherein even smaller capsules 84 are even more advantageous for optimally exploiting power.

The coil 81 has a curved shape so that a large amount of coil length is available in a relatively small space, and a high power density is accordingly achieved. FIG. 11 b) shows the coil 81 together with its envelope 83, wherein a distance is left in the schematic depiction between the envelope 83 and the coil 81 only for the sake of illustration. The envelope surrounds the volume 82 that the coil 81 assumes. The greatest linear extension of the envelope 92 runs between the two endpoints of the coil 81 in this case and hence is mostly outside of the envelope 83 of the coil 81. The greatest linear extension 92 however also describes the greatest, or respectively greatest possible linear distance between two points of the coil 81. Consequently, this greatest linear extension 92 is a linear measure of the compactness of the light-generating region of the micro-incandescent lamp 20. Especially in an imaging optical system, a very small greatest linear extension 92 is advantageous because a majority of the generated light can be arranged in the focal point of the imaging optical system so that light loss can be avoided. This translates to the benefit of the signal-to-noise ratio and the battery life.

At the same time, a corresponding coil 81 has a very small thermal mass so that the coil is heated to the operating temperature within fractions of a second, and a modulation of several hundred ° C. is feasible given a sufficient frequency for a time-resolved measurement of the change of a measuring gas concentration, for example for tracking the concentration of $CO_2$ in a breathing gas in the context of capnometry.

FIG. 11 c) shows the coil 81 from the narrow side. In this case, the thickness of the coil is the same as the smallest linear extension 94 of the envelope 83. FIG. 11 d) shows an alternative coil 81' that, in contrast to the coil 81, is straight and not bent. The envelope 83' in this case is basically cylindrical, and the greatest linear extension of the envelope lies within the coil 81'. While the absolute length of the coils is the same, the linear extension of the coil 81' is therefore greater than in the case of the coil 81 presented beforehand. A bend in the coil is therefore advantageous in the context of the present invention in order to generate high light intensity from a small overall volume.

The above-presented exemplary embodiments each present the ideal case of an assembly for example with division by a transmission lattice or a reflection lattice that is always spectrally neutral, a double bandpass filter assembly, and an assembly for the nonlinear analysis. These assemblies can however also be combined with each other so that the nonlinear analysis can for example also be used in a double bandpass filter assembly, or an assembly with a spectrally neutral lattice and a plurality of receivers. Likewise, a double bandpass filter assembly can be combined with spectrally neutral transmission lattices or reflection lattices and a plurality of detectors in order for example to perform an analysis with respect to a plurality of target gases.

All named features, including those taken from the drawings alone as well as individual features that are disclosed in combination with other features, are considered, alone and in combination, to be essential for the invention. Embodiments according to the invention can be fulfilled by individual features or a combination of several features. In the scope of the invention, features which are designated by "in particular" or "preferably" are understood to be optional features.

LIST OF REFERENCE SIGNS

10 Assembly
12 Measuring cell
14 Gas inlet
15 Gas inlet opening
16 Gas outlet
17 Gas outlet opening
18 Evaluation apparatus
20 Micro-incandescent lamp
20' Expanded light source
21 Evacuated glass bulb
22 Reflector
24 Filter for gas channel
25 Detector for gas channel
26 Filter for reference channel
27 Detector for reference channel
28, 28', 28" Detectors
30 IR photodiode
32 Reflector
34 Lost light components
40 Spectrally neutral transmission lattice
41 Spectrally neutral focusing transmission lattice
42 Spectrally neutral transmission lattice
50-54 Spectrally neutral reflection lattice
60 Control apparatus
62 Control unit
64 Photodiode
66 Amplifier
68 Amplifier for current measurement
69 Amplifier for voltage measurement
70 Multiplier
81 Coil
82 Volume
83, 83' Envelope
84 Capsule
85 Vacuum
86 Supply conductor
87 Base
88 Contact pin
90 Diameter of the encapsulation
92 Greatest linear extension of the envelope
94 Smallest linear extension of the envelope
110 Assembly
112 Interference
114, 114' Image of the interference
210 Assembly
212 Double bandpass filter
310 Assembly
312 Check valve
314 Pressure gauge
316 Gas reservoir
318 Pump
320 Controller for the pump
322 Motor

What is claimed is:
1. An assembly for measuring a gas concentration by means of absorption spectroscopy, the assembly comprising;
an IR light emitting thermal light source,
a measuring cell with a gas mixture to be analyzed, the measuring cell having a gas inlet and a gas outlet configured flor flowing the measuring gas therebe- tween, the measuring cell defining a measuring path in which the IR light crosses the gas to be measured,
one or more sensors,
one or more bandpass filters upstream from the one or more sensors,
an optical beam path comprising the thermal light source, the measuring cell including the measuring path, the one or more bandpass filters and the one or more sensors.
a gas concentration measuring evaluation apparatus in communication with the one or more sensors to determine a concentration of the measuring gas as a result of attenuation of the IR light in the measuring cell,
wherein the one or more bandpass filters comprises at least one measuring wavelength bandpass filter configured to transmit the IR light within a measuring wavelength range in which the gas to be measured absorbs IR light, and at least one reference wavelength bandpass filter configured to transmit IR light in a reference wavelength range in which the gas to be measured does not absorb IR light or only absorbs a slight amount in comparison to the measuring wavelength range,
further wherein the thermal light source comprises an encapsulated micro-incandescent lamp with a light-generating coil disposed is in a substantially transparent capsule, the capsule being evacuated or filled with an inert gas, and
wherein the measuring gas concentration is capnometric measurement of the proportion of $CO_2$ in breathing air.

2. The assembly according to claim 1, wherein the encapsulation of the micro-incandescent lamp has a diameter of less than 2 mm, less than 1.5 mm, or less than 1 mm.

3. The assembly according to claim 1, wherein a greatest linear distance between two points of the coil is less than 1 mm, or less than 0.5 mm.

4. The assembly according to claim 1, wherein an envelope of the coil in a direction of projection in which the envelope assumes a maximum envelope projection surface has a maximum envelope projection surface of less than 0.1 mm$^2$, or less than 0.02 mm$^2$.

5. The assembly according to claim 1, wherein at least one sensor is an infrared-sensitive photodiode comprising a sensitive surface of less than 1 mm$^2$, or less than 0.15 mm$^2$.

6. The assembly according to claim 1, further comprising a control apparatus for power-controlled driving and/or modulation of the micro-incandescent lamp,
wherein the control apparatus forms a product from current measured at the micro-incandescent lamp and measured voltage in order to determine an actual value of the emitted power, and/or is signal-linked to a photodiode arranged in the micro-incandescent lamp that receives a part of the light generated by the micro-incandescent lamp.

7. The assembly according to claim 1, wherein the IR light is guided bundled through the measuring cell and distributed to two or more sensors after passing through the measuring cell by means of a spectrally neutral optical plane-parallel or curved transmission or reflection lattice,
wherein the transmission lattice or reflection lattice has a lattice constant that is less by a factor of 30 or more, or by a factor of 50 and more than a diameter of a light spot on the transmission and reflection lattice.

8. The assembly according to claim 1, wherein the measuring cell comprises a tube, the inside of which is diffuse or has a high-gloss reflection on one end of which the micro-incandescent lamp is arranged, and on the other end of which the sensor or sensors with the upstream bandpass filters are arranged.

9. The assembly according to claim 1, wherein the at least one bandpass filter is designed as a double bandpass filter that lets IR light pass through both in the measuring wavelength range as well as in the reference wavelength range, wherein the double bandpass filter is upstream from an individual sensor, wherein the control apparatus is designed and configured to modulate the micro-incandescent lamp between an operating point with a lower output and an operating point with a higher output in which the respective emission spectrum has different component ratios in the measuring wavelength range and in the reference wavelength range.

10. The assembly according to claim 1, further comprising a pump and/or one or more switchable valves that are configured for temporarily increasing the pressure and/or reducing the pressure of the gas mixture in the measuring cell.

11. A method for measuring a gas concentration by means of absorption spectroscopy according to claim 1 in which the IR light is guided from the thermal light source through the measuring cell with the gas mixture to be analyzed, and the gas concentration of the gas to be measured that is contained in the gas mixture is determined by measuring the attenuation of the IR light introduced into the measuring cell caused by absorption by the gas to be measured,
wherein the thermal light source is designed as an encapsulated micro-incandescent lamp with a light-generating coil, wherein a sensor or several sensors are designed as infrared-sensitive photodiodes with a sensitive surface that is less than 1 mm$^2$, or less than 0.15 mm$^2$.

12. The method according to claim 11, wherein the micro-incandescent lamp is modulated with a measurement repetition frequency $f_{Mess}$ that is greater than 10 Hz or greater than 25 Hz, wherein a temperature of the coil is greater than 400° C. during measurement, and has a temperature modulation rise of at least 300° C., or at least 500° C., or exceeds 1000° C. at a maximum.

13. The method according to claim 11, wherein the micro-incandescent lamp is operated with power control.

14. The method according to claim 11, wherein over the course of measuring, the gas mixture pressure in the measuring cell is increased and/or lowered sequentially over intervals in time and the absorption is measured depending on the pressure, wherein to change the pressure, in particular, an outflow of the gas mixture is interrupted, and/or an inflow or an outflow of the gas mixture is supported and increased by a pump.

15. The method for measuring a gas concentration by means of absorption spectroscopy according to claim 11, in the assembly in which the IR light is conducted from the thermal light source through the measuring cell with the gas mixture to be analyzed, and the gas concentrations of the gas to be measured that is contained in the gas mixture is determined by measuring an attenuation of the light introduced into the measuring cell caused by absorption by the gas to be measured,
wherein over the course of measuring, the gas mixture pressure in the measuring cell is increased and/or lowered sequentially over intervals in time, or fluctuations in the gas mixture pressure are measured, and the absorption is measured depending on the pressure, wherein a pressure-dependent measuring series is analyzed with respect to components that are linearly and nonlinearly dependent on the pressure, and the component that is nonlinearly dependent on the pressure is used to measure the gas concentration of the gas to be measured, or to correct and/or calibrate a measurement of the gas concentration of the gas to be measured.

* * * * *